United States Patent [19]

Yoshida et al.

[11] 4,301,184
[45] Nov. 17, 1981

[54] FLAVORING WITH 5-METHYL-3,5-OCTADIEN-2-ONE

[75] Inventors: Takao Yoshida, West Long Branch; John B. Hall, Rumson, both of N.J.

[73] Assignee: International Flavors & Fragrances Inc., New York, N.Y.

[21] Appl. No.: 182,233

[22] Filed: Aug. 28, 1980

Related U.S. Application Data

[60] Continuation-in-part of Ser. No. 90,749, Nov. 2, 1979, abandoned, which is a division of Ser. No. 46,390, Jun. 7, 1979, Pat. No. 4,234,518, which is a division of Ser. No. 932,649, Aug. 10, 1978, Pat. No. 4,169,109.

[51] Int. Cl.$^3$ .................................... A23L 1/226
[52] U.S. Cl. .................................... 426/534; 426/538
[58] Field of Search .................................... 426/534

[56] References Cited

U.S. PATENT DOCUMENTS 4,169,109 9/1979 Yoshida et al. ............ 568/378 X
4,234,518 11/1980 Yoshida et al. ............ 568/378 X

OTHER PUBLICATIONS

Chemical Abstracts, vol. 73, 1970, p. 130585n.

Primary Examiner—Joseph M. Golian
Attorney, Agent, or Firm—Arthur L. Liberman

[57] ABSTRACT

Described is a process for augmenting or enhancing the aroma or taste of foodstuffs comprising adding to a foodstuff an aroma or taste augmenting or enhancing quantity of 5-methyl-3,5-octadien-2-one produced according to the process of reacting 2-methyl-2-pentenal with acetone in the presence of a zinc acetate dihydrate catalyst.

2 Claims, 3 Drawing Figures

IR SPECTRUM FOR EXAMPLE IV, FRACTION 8.

FIG.I
GLC PROFILE FOR EXAMPLE IV.

NMR SPECTRUM FOR EXAMPLE IV, FRACTION 8.

IR SPECTRUM FOR EXAMPLE IV, FRACTION 8.

FLAVORING WITH 5-METHYL-3,5-OCTADIEN-2-ONE

This application is a continuation-in-part of application for United States Letters Pat. Ser. No. 090,749, now abandoned which in turn is a divisional of application for United States Letters Patent Ser. No. 046,390 filed on June 7, 1979, now U.S. Pat. No. 4,234,518 issued on Nov. 18, 1980 which, in turn, is a divisional of application for United States Letters Patent Ser. No. 932,619 filed on Aug. 10, 1978, now U.S. Pat. No. 4,169,109 issued on Sept. 25, 1979.

BACKGROUND OF THE INVENTION

The invention relates to a process for the production of ketones unsaturated in the alpha, beta position to the carbonyl group by reacting an aldehyde with a ketone in the presence of a catalyst consisting essentially of either of zinc acetate or zinc acetate dihydrate.

The use of zinc acetate in carrying out such reactions has heretofore been unknown and is not obvious from the teachings of the prior art. Thus, Houben-Weyl, "Methoden der Organischen Chemie", volume 7/1, pages 77 et. seq. and "Organic Reactions", volume 16, pages 27 to 47, 69 to 78 and 177 et seq. disclose the fact that aldehydes and ketones can be converted to alpha, beta unsaturated ketones. Temperatures of from 5° C. up to 100° C. are preferred for this aldol condensation ("Organic Reactions," loc. cit., page 77). The numerous catalysts used in these methods, for example alkali and alkaline earth metal hydroxides, organic bases, alkali metal salts and alcoholates promote auto-condensation of the aldehydes and ketones and therefore causes the formation of large amounts of by-products in most cases.

Furthermore, the U.S. Pat. No. 4,005,147 discloses the production of alpha, beta unsaturated ketones by reacting in the liquid phase an aldehyde with a ketone in the presence of a catalyst consisting essentially of zinc oxide.

It is furthermore known from U.S. Pat. No. 2,549,508 that aldehydes and ketones can be converted into unsaturated ketones of high molecular weight in the gas phase at temperatures of from 500° to 1000° C. in the presence of a catalyst consisting essentially of zinc oxide and from 1 to 15% by weight of zirconium oxide. In this process, however, only low conversions and low yields are achieved. Moreover high expenditure for equipment is required for reactions in the presence of hydrogen at the said temperatures for safety reasons. Moreover cracking processes take place at the surface of the catalyst in such reactions and these have a negative effect on the life of the catalyst.

The reaction of two identical or different aldehydes or ketones in the liquid phase at elevated temperature and in the presence of a catalyst (obtained by calcining a mixture of molybdenum oxide, magnesium oxide with or without zinc oxide or compounds of these metals) to form alpha, beta-unsaturated aldehydes or ketones is known from German Pat. No. 1,203,243.

According to the method described in the said patent good conversions and very good yields of alpha, beta-unsaturated aldehydes are obtained in the condensation of aldehydes with one another, particularly, in the condensation of n-butyraldehyde or 2-ethylhexenal.

The process of German Pat. No. 1,203,243 is not so suitable for the reaction of aldehydes with ketones to form alpha, beta-unsaturated ketones, considerably lower conversions and selectivities being achieved. This is particularly noticeable when not only isobutyraldehyde (i.e., and aldehyde which does not undergo auto-condensation) is reacted with a ketone by the method of the said German patent, but also when aldehydes are used which readily undergo autocondensation, as for example 3,3-dimethylacrolein and citral.

Nothing in the prior art however implies the process of our invention using either a zinc acetate catalyst or a zinc acetate dihydrate catalyst whereby certain ketones may be produced in a convenient, sufficient and economical manner.

THE INVENTION

Figure 1:
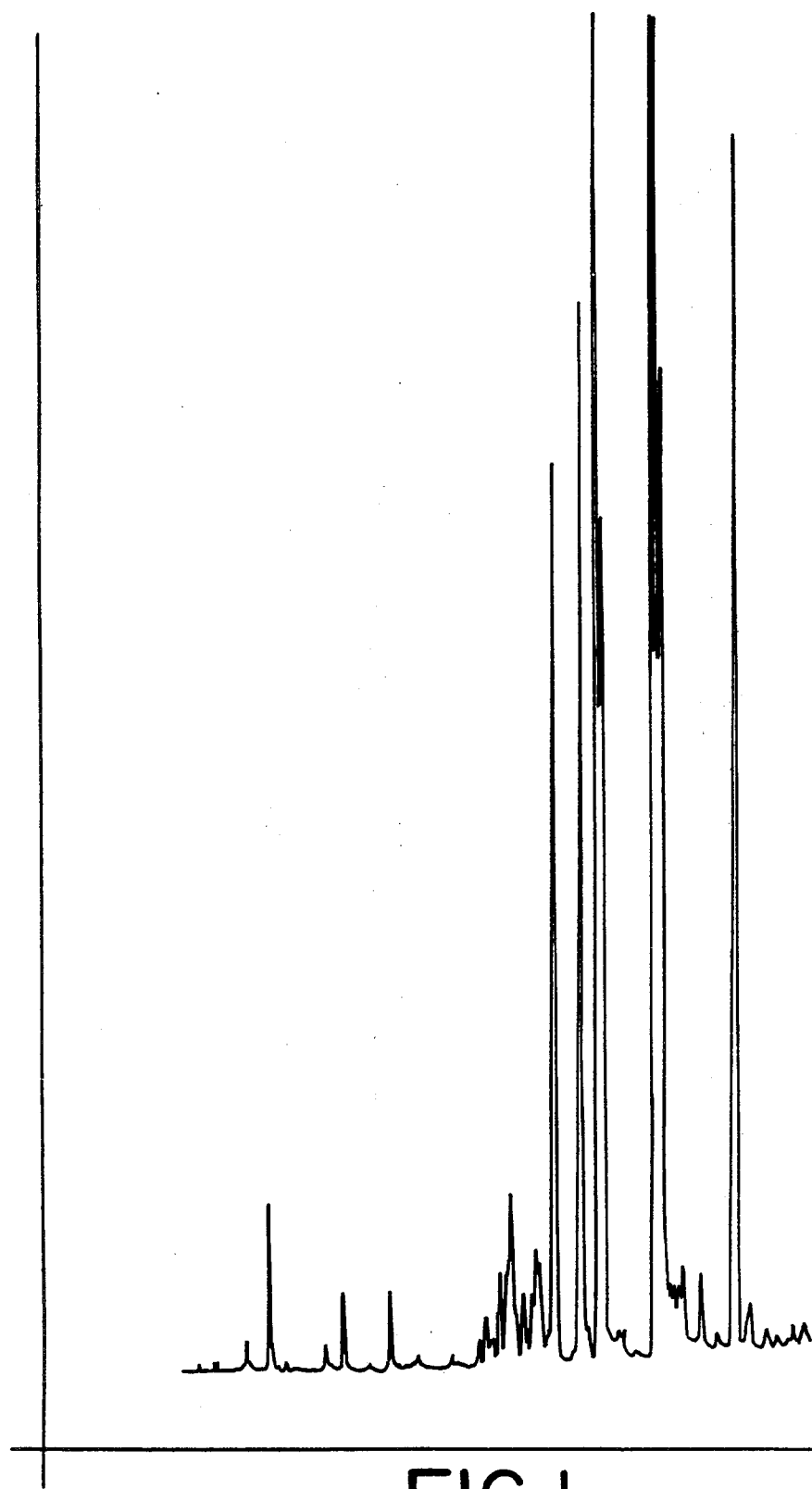
FIG. 1 is the GLC profile for the reaction product produced according to Example I.

This invention covers a process which enables aldehydes, particularly aldehydes having a tendency for autocondensation to be reacted selectively with ketones to alpha, beta unsaturated ketones with good conversions and excellent yields.

More specifically our invention covers the following reaction schemes:

Scheme "A"

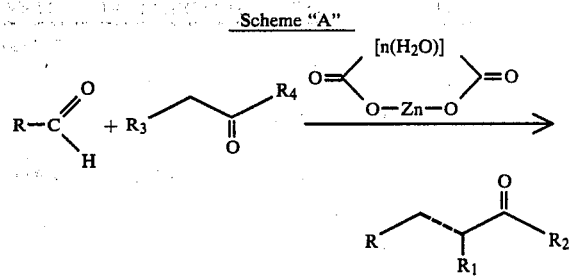

wherein the dashed line represents a cis or trans carbon-carbon double bond and n=0 or 2

Scheme "B"

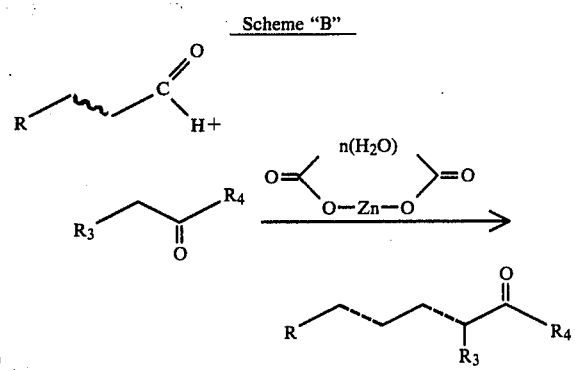

wherein the wavy line and each of the dashed lines represent cis or trans carbon-carbon double bonds and n=0 or 2; and wherein R is lower alkyl having from one up to about five carbon atoms; aralkyl having seven or eight carbon atoms; alkenyl having from three up to twelve carbon atoms; alkadienyl having from eight up to twelve carbon atoms; alkyl cycloalkenyl alkyl having from eight up to ten carbon atoms; alkyl alkenyl having from seven up to nine carbon atoms and aralkyl having seven or eight carbon atoms; wherein $R_1$ and $R_3$ are each the same or different and each represents hydrogen or lower alkyl having from one up to five carbon atoms; and wherein $R_2$ and $R_4$ are each the same or different and each represents lower alkyl having from one up to five carbon atoms.

The use of zinc acetate and zinc acetate dihydrate gives rise to unexpected, unobvious and advantageous results and also gives rise to novel compounds heretofore not made particularly in view of their apparent difficulty of manufacture.

In the above stated reduction schemes the mole ratio of catalyst:ketone reactant may vary from about 0.05:1 up to about 1:1 with a preferable mole ratio of catalyst:ketone reactant being about 0.2:1.

In the above mentioned reaction sequences the mole ratio of ketone-aldehyde reactants may vary from about 1:1 up to about 10:1 with a preferable mole ratio of ketone:aldehyde reactant being from about 3 up to about 5.

In each of the above mentioned reaction sequences the temperature may vary from about 100° C. up to about 250° C. with a preferable reaction temperature being in the range of from 130° C. up to 200° C.

Although the above mentioned reactions may be carried out at atmospheric pressure it is preferred to carry out these reactions in equipment which can withstand higher pressures; particularly a pressure buildup of the order of from about 100 up to about 400 psig.

Previously mentioned bases such as sodium hydroxide or potassium hydroxide and zinc oxide (100% pure) were used for catalysis of aldol condensations whereby undesired self condensation products were produced (such as mesityl oxide in the case of acetone which is difficult to remove from the product of reaction, in the case of, for example, 3-penten-2-one). According to our invention a minimal quantity of self condensation product results.

More specifically in the case of the reaction involving acetaldehydes and methyl ethyl ketone reactants using a zinc oxide catalyst the product ratio of 4-hexen-3-one to 3-methyl-3-penten-2-one is 6.3:37 with a yield of about 13%. Whereas U.S. Pat. No. 4,005,147 teaches the requirement of application of high pressures to the reaction mass, our invention does not require such immediate application of pressure to the reaction mass although it is generally convenient to carry out the reaction in vessels that can withstand pressures of from about 100 up to about 400 psig.

The following table is a summary of specific examples carried out:

| KETONE REACTANT | ALDEHYDE REACTANT | REACTION TEMPERATURE | TIME | MAIN CONSTITUENT(S) OF REACTION PRODUCT | YIELD(%) |
|---|---|---|---|---|---|
| [structure] | [structure] | 140° C. | 3 Hours | [structures] | 43 |
| [structure] | [structure] | 130–140° C. | 6 Hours | [structures] | 38 |
| [structure] | [structure] | 190° C. | 12 Hours | [structures] Mixture wherein in each molecule one of the dashed lines is a carbon—carbon single bond and the other of the dashed lines is a cis or trans carbon—carbon double bond. | 35 |
| [structure] | [structure] | 150° C. | 3 Hours | [structure] Wherein one of the dashed lines is a carbon—carbon single bond and the other of the dashed llines is a cis or trans carbon—carbon double bond | 12 |

-continued

| KETONE REACTANT | ALDEHYDE REACTANT | REACTION TEMPERATURE | TIME | MAIN CONSTITUENT(S) OF REACTION PRODUCT | YIELD(%) |
|---|---|---|---|---|---|
| (methyl ethyl ketone structure) | (methylcyclohexenyl carboxaldehyde) | 160° C. | 8 Hours | (product structures) + Wherein one of the dashed lines is a carbon—carbon single bond and the other of the dashed lines is a cis or trans carbon—carbon double bond. | 45 |
| (methyl isobutyl ketone structure) | (methylcyclohexenyl carboxaldehyde) | 160° C. | 8 Hours | (product structures) + | 32 |
| acetone | (4-methylcyclohexenyl carboxaldehyde) | 180° C. | 7 Hours | (product structure) Wherein one of the dashed lines is a carbon—carbon single bond and the other of the dashed lines is a cis or trans carbon—carbon double bond. | 47 |
| methyl ethyl ketone | (4-methylcyclohexenyl carboxaldehyde) | 150° C. | 10 Hours | (product structures) + Wherein one of the dashed lines is a carbon—carbon single bond and the other of the dashed lines is a cis or trans carbon—carbon double bond. | 57 |
| methyl ethyl ketone | (branched aldehyde with cyclohexyl) | 190° C. | 8 Hours | (product structures) + (Mixture of compounds wherein one of the dashed lines is a cis or trans carbon—carbon double bond and the other of the dashed lines is a carbon—carbon single bond; and wherein one of the wavy lines is a carbon—carbon single bond and the other of the wavy lines is a carbon—carbon double bond. | 56 |
| acetone | (α-methylphenylacetaldehyde) | 150–165° C. | 10 Hours | (product structure) Wherein one of the dashed lines is a carbon—carbon single bond and the other of the dashed lines is a cis or trans carbon—carbon double bond. | 54 |
| methyl ethyl ketone | (α-methylphenylacetaldehyde) | 150–170° C. | 10 Hours | (product structures) + Wherein one of the dashed lines is a carbon—carbon single | 59 |

-continued

| KETONE REACTANT | ALDEHYDE REACTANT | REACTION TEMPERATURE | TIME | MAIN CONSTITUENT(S) OF REACTION PRODUCT | YIELD(%) |
|---|---|---|---|---|---|
| (acetone) | (crotonaldehyde + acrolein) | 135° C. | 3.5 Hours | bond and the other of the dashed lines is a cis or trans carbon—carbon double bond. | 34 |
| (acetone) | (methyl-substituted unsaturated aldehydes) | 170–180° C. | 5 Hours | Mixture wherein the dashed lines represent cis or trans carbon—carbon double bond. | 34 |

Mixture wherein each of the dashed lines represents cis or trans carbon—carbon double bonds Examples of three of the reaction products prepared herein which are useful particularly for their organoleptic properties are set forth in the following Table II:

TABLE II

| NAME & STRUCTURE OF MATERIAL | PERFUME PROPERTIES | FOOD FLAVOR PROPERTIES | TOBACCO FLAVOR PROPERTIES |
|---|---|---|---|
| 5-Methyl-3,5-octadien-2-one (Mixture wherein each of the dashed lines represents cis or trans carbon-carbon double bond.) | At 10% in Food Grade Alcohol a powerful, spicy, nutty, (walnut) aroma with a fruity (citrusy, melony) character. | Sweet, nutty, woody, cinnamon like aroma with a sweet, nutty, woody, cinnamon, nut meat-like character at 3ppm; useful in cinnamon and nut meat-flavor foodstuffs. | |
| 3-Methyl-5-(2,6,6-trimethyl-1(and 2)-cyclohexen-1-yl)-3(and 4)-penten-2-one (Mixture of compounds wherein one of the dashed lines is a cis or trans carbon—carbon double bond and the other of the dashed lines is a carbon—carbon single bond; and wherein one of the wavy lines is a carbon—carbon single bond and the other of the wavy lines is a carbon—carbon double bond.) | A buttery, woody-ionone like aroma with a sour berry nuance. | A floral/ionone aroma character and floral/ionone flavor character at 2ppm. | |

TABLE II-continued

| NAME & STRUCTURE OF MATERIAL | PERFUME PROPERTIES | FOOD FLAVOR PROPERTIES | TOBACCO FLAVOR PROPERTIES |
|---|---|---|---|
| 4-(4-Methyl-3-cyclohexene-1-yl)-3-buten-2-one<br><br>Mixture of comps. wherein one of the dashed lines is a carbon—carbon single bond and the other of the dashed lines is a cis or trans carbon—carbon double bond.) | At 10% in Food Grade Ethanol the cis isomer has a green, herbaceous, melony nuance; the trans isomer has a sweet, fatty, green spicy aroma; together the cis & trans isomer mixture has a green, herbaceous spicy, melony aroma with a woody undertone. | The mixture of cis and trans isomers at 0.2ppm has a green, floral, sandalwood-like, geranium like, spicy and citrusy aroma characteristic with a green, floral, sandalwoody-like, geranium, spicy and citrusy flavor characteristic. | |

When the ketones of our invention are used as food flavor adjuvants the nature of the co-ingredients included with the ketones used in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soaps, convenience foods, beverages, dairy products, candies, chewing gums, vegetables, cereals, soft drinks, snacks and the like.

As used herein, the term "medicinal product" includes both solids and liquids which are ingestible, non-toxic materials which have medicinal value such as cough syrups, cough drops, aspirin and chewable medicial tablets.

The term "chewing gum" is intended to mean a composition which comprises a substantially water insoluble, chewable plastic gum base such as chicle or substitutes therefor including jelutong, guttakay, rubber or certain comestible natural or synthetic resins or waxes. Incorporated with the gum base in admixing therewith may be plasticizers or softening agents, e.g., glycerine; and a flavoring composition which incorporates one or more of the ketones made according to the process of our invention, and in addition, sweetening agents which may be sugars, including sucrose or dextrose and/or artificial sweeteners such as cyclamates, saccharin or dihydrochalcones. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials, lipids; carbohydrates; starches, pectins and emulsifiers, e.g., mono- and diglycerides of fatty acids, skim milk powder, hexoses, pentoses, disaccharides, e.g., sucrose corn syrup and the like.

Conditioners include compounds such as bleaching and maturing agents, e.g., benzoyl peroxide, calcium peroxide, hydrogen peroxide and the like; starch modifiers such as peracetic acid, sodium chloride, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caprioc acid, caprylic acid, cinnamic acid, isobutyric acid, isovaleric acid, alpha-methyl-butyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta, beta-dimethylacrolein, methyl-n-amyl ketone, n-hexenal, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanol; alcohols such as 1-butanol, benzyl alcohol, 1-borneol, trans-2-buten-1-ol, ethanol, geraniol, 1-hexanal, 2-heptanol, trans-2-hexenol-1, cis-3-hexan-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methyl-butyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alphapinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as $\epsilon$-nonalactone; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether similulated or natural, and should, in any event, (i) be organoleptically compatible with the ketone(s) produced according to the process of our invention by not covering or spoiling the organoleptic properties (aroma and/or taste) thereof; (ii) be non-reactive with the ketone(s) produced according to the process of our invention and (iii) be capable of providing an environment in which the ketone(s) produced according to the process of our invention can be dispersed or admixed to provide a homogeneous medium. In addition, selection of one or more flavoring adjuvants, as well as the quantities thereof will depent upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of sold products, e.g., simulated foodstuffs, ingredients capable of providing normally solid compositions should be selected such as various cellulose derivatives.

As will be appreciated by those skilled in the art, the amount of the ketone(s) produced according to the process of our invention employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective i.e., sufficient to alter, modify or enhance the organoleptic characteristics of the parent composition, whether foodstuff per se, chewing gum per se, medicinal product per se, toothpaste per se, or flavoring composition.

The use of insufficient quantities of the ketone(s) produced according to the process of our invention will, of course, substantially vitiate any possibility of obtaining the desired results while excess quantities prove needlessly costly and in extreme cases, may disrup the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of the ketone(s) produced according to the process of our invention ranging from a small but effective amount, e.g., 0.02 parts per million up to about 100 parts per million based on total composition are suitable. Concentrations in excess of the maximum quantity stated are not normally recommended, since they fail to prove commensurate enhancement of organoleptic properties. In those instances, wherein the ketone(s) produced according to the process of our invention is added to the foodstuff as an integral component of a flavoring composition, it is, of course, essential that the total quantity of flavoring composition employed be sufficient to yield an effective concentration of the ketone(s) produced according to the process of our invention in the foodstuff product.

Food flavoring compositions prepared in accordance with the present invention preferably contain the ketone(s) produced according to the process of our invention in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the compound ketone(s) produced according to the process of our invention with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and the ketone(s) produced according to the process of our invention in a dry blender until the requisite degree of uniformity is achieved.

It is presently preferred to combine with the ketone(s) produced according to the process of our invention the following adjuvants:

p-Hydroxybenzyl acetone;
Geranoil;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamm-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-gentenal diethyl acetal;
beta-Damascone (1-crotonyl-2,6,6-trimethylcyclohex-1-ene;
beta-Damascenone (1-crotonyl-2,6,6-trimethyl-1,3 cyclohexadiene);
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene); and
2-(4-Hydroxy-4-methylpentyl) norbornadiene prepared according to U.S. Pat. No. 3,886,289, issued on May 27, 1975.

The ketone(s) produced according to the process of our invention and one or more auxiliary perfume ingredients, including for example, alcohols, aldehydes, ketones other than the ketone(s) produced according to the process of our invention, terpinic hydrocarbons, nitriles, esters, lactones, natural essential oils and synthetic essential oil, may be admixed so that the combined odors of the individual components produce a pleasant and desired fragrance, particularly and preferably in rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, the ketone(s) produced according to the process of our invention can be used to alter, modify or enhance the aroma characteristics of a perfume composition, for example, by utilizing or moderating the olfactory reaction contributed by another ingredient in the composition.

The amount of the ketone(s) produced according to the process of our invention which will be effective in perfume compositions as well as in perfumed articles and colognes depends on many factors, including the other ingredients, their amounts and the effects which are desired. It has been found that perfume compositions containing as little as 0.01% of the ketone(s) produced according to the process of our invention or even less (e.g. 0.005%) can be used to impart a spicy, nutty, citrusy and/or sandalwood aromas to soaps, cosmetics or other products. The amount employed can range up to 70% of the fragrance components and will depend on considerations of cost, nature of the end product, the effect desired on the finished product and the particular fragrance sought.

The ketone(s) produced according to the process of our invention is useful (taken alone or together with the other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders and the like. When used as (an) olfactory component(s) as little as 1% of the ketone(s) produced according to the process of our invention will suffice to impart intense spicy, nutty, citrusy and/or sandalwood notes to woody formulations. Generally, no more than 3% of the ketone(s) produced according to the process of our invention, based on the ultimate end product, is required in the perfume composition.

In addition, the perfume composition or fragrance composition of our invention can contain a vehicle, or carrier for the ketone(s) produced according to the process of our invention. The vehicle can be a liquid such as a non-toxic alcohol, a non-toxic glycol, or the like. The carrier can also be an absorbent solid, such as a gum (e.g., gum arabic) or components for encapsulating the composition (such as gelatin).

It will thus be apparent that the ketone(s) prepared according to the process of our invention can be utilized to alter, modify or enhance sensory properties, particularly organoleptic properties, such as flavor(s) and/or fragrance(s) of a wide variety of consumable materials.

Furthermore, the ketone(s) produced according to the process of our invention are capable of supplying and/or potentiating certain flavor and aroma notes usually lacking in many tobacco flavors heretofore provided.

As used herein in regard to tobacco flavors, the terms "alter" and "modify" in their various forms means "supplying or imparting flavor character or note to otherwise bland tobacco, tobacco substitutes, or tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of tobacco or a tobacco substitute or a tobacco flavor.

Our invention thus provides an organoleptically improved smoking tobacco product and additives thereof, as well as methods of making the same which overcome specific problems heretofore encountered in which specific desired Virginia-type tobacco aroma and taste nuances thereof, are created or enhanced and may be readily controlled and maintained at the desired uniform level regardless of variations in the tobacco components of the blend.

This invention further provides improved tobacco additives and methods whereby various Virginia-type tobacco notes may be imparted to smoking tobacco products and may be readily varied and controlled to product the desired uniform flavor characteristics.

In carrying out this aspect of our invention, we add to smoking tobacco materials or a suitable substitute therefor (e.g., dried lettuce leaves) an aroma and flavor additive containing as an active ingredient a ketone(s) produced according to the process of our invention.

In addition to the ketone(s) produced according to the process of our invention, other flavoring and aroma additives may be added to the smoking tobacco materials or substitute therefor either separately or in mixture with the ketone(s) produced according to the process of our invention as follows:

(i) Synthetic Materials:
Beta-ethyl-cinnamaldehyde;
Beta-cyclohomocitral;
Eugenol;
Dipentene;
Beta-Damascenone;
Beta-Damascone;
Maltol;
Ethyl Maltol;
Delta-undecalactone;
Delta-decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethylnaphtho-[2,1-b]-furan;
4-Hydroxy hexanoic acid, gamma lactone; and
Polyisoprenoid hydrocarbons defined in Example V of U.S. Pat. No. 3,589,372, issued on June 29, 1971.

(ii) Natural Oils:
Celery seed oil;
Coffee extract;
Bergamot Oil;
Cocoa extract;
Nutmeg Oil;
Origanum Oil.

An aroma and flavoring concentrate containing ketone(s) produced according to the process of our invention and, if desired, one or more of the above-indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of the ketone(s) produced according to the process of our invention to smoking tobacco material is between 250 ppm and 1,500 ppm (0.025%–0.15%) of the active ingredients to the smoking tobacco material. We have further found that satisfactory results are obtained if the proportion by weight of the sum total of the ketone(s) produced according to the process of our invention used to flavoring material is between 2,500 and 15,000 ppm (0.25%–1.5%).

Any convenient method for incorporating the ketone(s) produced according to the process of our invention in the tobacco product may be employed. Thus, the ketone(s) produced according to the process of our invention taken alone or along with other flavoring additives may be dissolved in a suitable solvent such as ethanol, pentane, diethyl ether and/or other volatile organic solvents and the resulting solution may either be sprayed on the cured, cased and blended tobacco material or the tobacco material may be dipped into such solution. Under certain circumstances, a solution of the ketone(s) produced according to the process of our invention taken alone or taken further together with other flavoring additives as set forth above, may be applied by means of a suitable applicator such as a brush or roller on the paper or leaf wrapper for the smoking product, or it may be applied to the filter by either spraying, or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the ketone(s) produced according to the process of our invention in excess of the amounts or concentrations above-indicated so that when blended with other tobaccos, the final product will have the percentage within the indicated range.

In accordance with one specific example of our invention, an aged, cured and shredded domestic burley tobacco is sprayed with a 20% ethyl alcohol solution of 5-methyl-3,5-octadiene-2-one mixture of cis and trans isomers in an amount to provide a tobacco composition containing 800 ppm by weight of the 5-methyl-3,5-octadiene-2-one on a dry basis. Thereafter, the alcohol is removed by evaporation and the tobacco is manufactured into cigarettes by the usual techniques. The cigarette when treated as indicated has a desired and pleasing aroma (increased smoke body sensation in the mouth with enhanced tobacco-like notes and pleasant aromatic nuances) which is detectable in the main and side streams when the cigarette is smoked. This aroma is described as having sweet, fruity, Virginia tobacco like notes.

While our invention is particularly useful in the manufacture of smoking tobacco, such as cigarette tobacco, cigar tobacco and pipe tobacco, other tobacco products formed from sheeted tobacco dust or fines may also be used. Likewise, the ketone(s) produced according to the process of our invention can be incorporated with materials such as filter tip materials, seam paste, packaging materials and the like which are used along with tobacco to form a product adapted for smoking. Furthermore, the ketone(s) produced according to the process of our invention can be added to certain tobacco substitutes of natural or synthetic origin (e.g., dried lettuce leaves) and, accordingly, by the term "tobacco": as used throughout this specification is meant any composition intended for human consumption by smoking or otherwise, whether composed of tobacco plant parts or substitute materials or both.

The following art examples serve to illustrate our invention and the invention is to be considered restricted thereto only as indicated in the appended claims.

All parts and percentages given herein are by weight unless otherwise specified.

EXAMPLE I

Preparation of Mixture Containing Substantially 5-methyl-3,5-octadiene-2-one Into a 2 liter autoclave are charged 2-methyl-2-pentenal (196 grams), acetone (580 grams) and zinc acetate dihydrate. The reaction mixture is heated at 170°–180° C. for a period of 5 hours. After filtering the catalyst the organic layer is washed with 10% salt solution. Distillation and bulking fractions 4–8 gives 80.3 grams of product, B.P. 91°–98° C. at 5–7 mm Hg. pressure. The bulked fractions or separate fractions are useful for augmenting or enhancing the aroma or taste of the foodstuff.

More specifically, the distillation yields the following fractions:

| Fraction No. | Vapor Temp. (°C.) | Liquid Temp. (°C.) | mm/Hg Pressure | Weight of Fraction (g.) |
|---|---|---|---|---|
| 1 | 51/76 | 80/95 | 5/7 | 4.6 |
| 2 | 82 | 95 | 7 | 6.2 |
| 3 | 83 | 94 | 7 | 6.8 |
| 4 | 96 | 105 | 7 | 15.2 |
| 5 | 96 | 105 | 7 | 16.8 |
| 6 | 96 | 108 | 7 | 24.3 |
| 7 | 98 | 120 | 7 | 18.2 |
| 8 | 91 | 145 | 5 | 5.8 |

-continued

| Fraction No. | Vapor Temp. (°C.) | Liquid Temp. (°C.) | mm/Hg Pressure | Weight of Fraction (g.) |
|---|---|---|---|---|
| 9 | 90 | 180 | 3 | 2.5 |

As confirmed by NMR and IR analysis, fraction 8 of this distillation contains substantially all 5-methyl-3,5-octadien-2-one (84 parts 5-methyl-3,5-octadien-2-one and 2 parts, of a higher molecular weight compound probably having the structure:

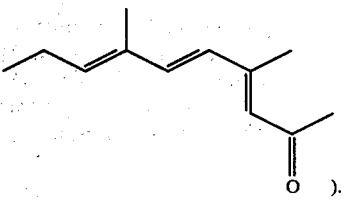

).

Fraction 5 is a fraction containing four peaks on the GLC profile of FIG. 1 of the drawings, to wit:

2 parts by weight of peak 2, which is for the compound having the structure:

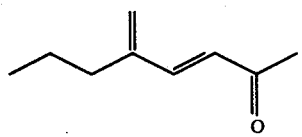

91 parts by weight of peaks 3 and 4 which are for the compound 5-methyl-3,5-octadien-2-one having the structure:

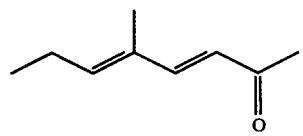

7 parts by weight of the compound probably having the structure:

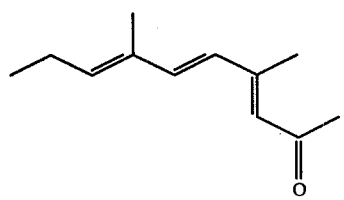

The distillation is carried out on a 8-plate Vigreux column.

Figure 2:
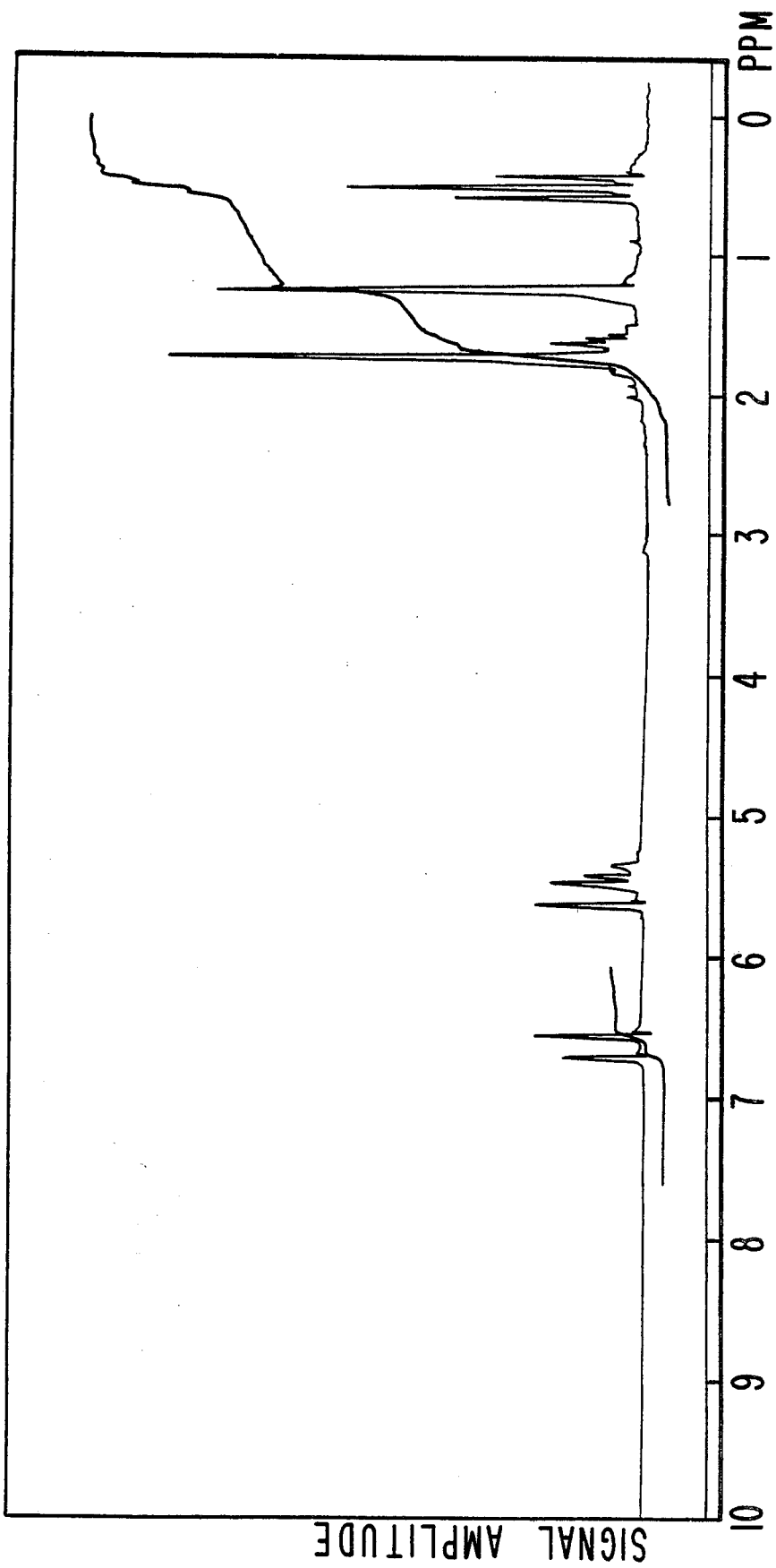
FIG. 2 is the NMR spectrum for 5-methyl-3,5-octadien-2-one produced according to Example I.
Figure 3:
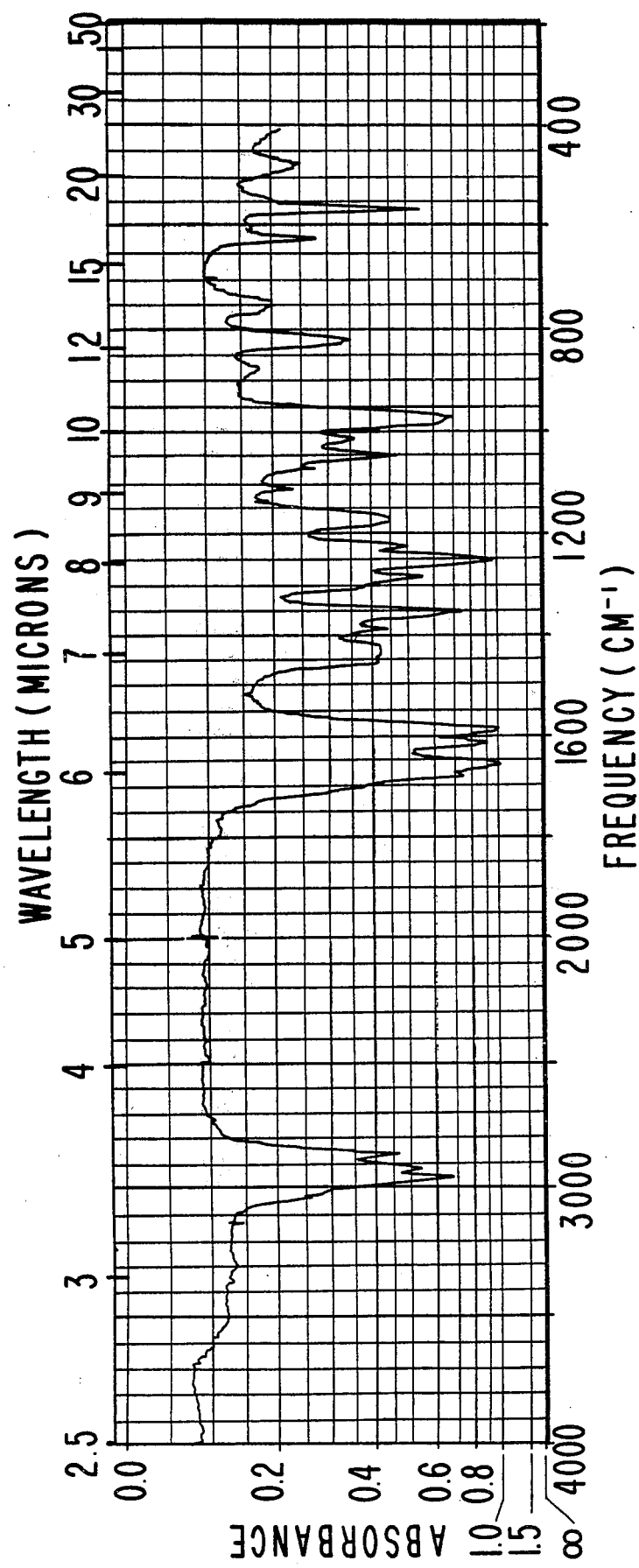
FIG. 3 is the infrared spectrum for 5-methyl-3,5-octadien-2-one produced according to Example I.

FIG. 1 is the GLC profile for the reaction mixture prior to distillation. FIG. 2 is the NMR spectrum for 5-methyl-3,5-octadien-2-one prepared according to the instant Example and which fraction 8 consists entirely of. The NMR spectrum is for fraction 8. FIG. 3 is the infrared spectrum for fraction 8 of the above-mentioned distillation which is 5-methyl-3,5-octadien-2-one.

EXAMPLE II

Cinnamon Flavor Formulation

A cinnamon-like butter formulation is prepared by admixing the following ingredients:

| Ingredients | Parts by Weight |
| --- | --- |
| Butter | 10 |
| Sucrose | 2 |
| Mixture consisting essentially of 5-methyl-3,5-octadien-2-one; fraction 5 of the distillation of Example 1 | 100 |

The 5-methyl-3,5-octadien-2-one-containing mixture (fraction 5 of the distillation of Example I) produced according to Example I enhances the sweet, nutty, woody and cinnamon characteristics of the cinnamon flavor and causes it to be more natural.

When fraction 8 consisting substantially entirely of 5-methyl-3,5-octadien-2-one is used to replace fraction 5 the same sweet, nutty, woody and cinnamon characteristics of the cinnamon flavor are enhanced and caused to be more natural.

What is claimed is:

1. A process for augmenting or enhancing the aroma or taste of a foodstuff comprising the step of adding to said foodstuff from 0.02 parts per million up to 100 parts per million based on the total weight of said foodstuff a composition comprising 5-methyl-3,5-octadien-2-one prepared by reacting 2-methyl-2-pentenal and acetone in the presence of a zinc acetate dihydrate catalyst at a temperature in the range of 170°–180° C. for a period of 5 hours and then fractionally distilling the resulting reaction product at a temperature in the range of 91°–98° C. at 5–7 mmHg pressure.

2. The process of claim 1 wherein the flavor augmented or enhanced is a cinnamon-flavor.

* * * * *